US008532253B2

(12) United States Patent
Virta

(10) Patent No.: US 8,532,253 B2
(45) Date of Patent: Sep. 10, 2013

(54) 3D MAMMOGRAPHY

(75) Inventor: Arto Virta, Helsinki (FI)

(73) Assignee: Planmed Oy, Helsinki (FI)

( * ) Notice: Subject to any disclaimer, the term of this patent is extended or adjusted under 35 U.S.C. 154(b) by 174 days.

(21) Appl. No.: 13/131,365

(22) PCT Filed: Nov. 30, 2009

(86) PCT No.: PCT/FI2009/050963
§ 371 (c)(1),
(2), (4) Date: May 26, 2011

(87) PCT Pub. No.: WO2010/061062
PCT Pub. Date: Jun. 3, 2010

(65) Prior Publication Data
US 2011/0222653 A1    Sep. 15, 2011

(30) Foreign Application Priority Data
Nov. 28, 2008  (FI) ...................................... 20080639

(51) Int. Cl.
*A61B 6/04* (2006.01)
(52) U.S. Cl.
USPC .......................................................... 378/37
(58) Field of Classification Search
USPC .................. 378/37, 39, 21, 62, 64, 197, 208
See application file for complete search history.

(56) References Cited

U.S. PATENT DOCUMENTS

| | | | | |
|---|---|---|---|---|
| 4,926,453 A * | 5/1990 | Toniolo | ............................ | 378/37 |
| 7,092,482 B2 * | 8/2006 | Besson | ............................ | 378/37 |
| 7,564,938 B2 * | 7/2009 | Tesic et al. | ........................ | 378/7 |
| 2004/0101096 A1 * | 5/2004 | Tsujii | ............................ | 378/37 |
| 2005/0113681 A1 | 5/2005 | DeFreitas et al. | | |
| 2005/0129172 A1 | 6/2005 | Mertelmeier | | |
| 2007/0140419 A1 | 6/2007 | Souchay | | |
| 2007/0198448 A1 | 8/2007 | Fokoue-Nkoutche et al. | | |
| 2008/0181361 A1 | 7/2008 | Eldered et al. | | |
| 2011/0228902 A1 * | 9/2011 | Virta | ............................. | 378/21 |

FOREIGN PATENT DOCUMENTS

| | | |
|---|---|---|
| EP | 0370089 | 5/1990 |
| EP | 1419735 | 5/2004 |
| WO | 88/01847 | 3/1988 |
| WO | 2005/051199 | 6/2005 |
| WO | 2006/058160 | 6/2006 |
| WO | 2007/050025 | 5/2007 |

OTHER PUBLICATIONS

Design and Performance of the Prototype Full Field Breast Tomosynthesis System With Selenium Based Flat Panel Detector, Baorui Ren et al., Medical Imaging 2005, Physics of Medical Imaging, 12 pages.

* cited by examiner

*Primary Examiner* — Irakli Kiknadze
(74) *Attorney, Agent, or Firm* — Cozen O'Connor

(57) ABSTRACT

The present invention relates to 3D mammography, in which individual images of a breast are taken at different projection angles and a 3D image subsequently synthesized from this image information. According to the invention, a breast to be imaged is arranged locked in a locking means (16, 17) and during the imaging process, the x-ray source (13) is continuously moved with respect to location of the breast and the breast is irradiated at a number of angular positions of the x-ray source (13). During an irradiation period of the imaging process, the locking means (16, 17) is turned as synchronized with the movement of the x-ray source (13). The imaging process preferably further includes such non-irradiation periods during which the locking means (16, 17) is turned in a direction opposite to that when turned as synchronized with the movement of the x-ray source (13) during an irradiation period.

18 Claims, 4 Drawing Sheets

3D MAMMOGRAPHY

FIELD OF THE INVENTION

The present invention relates to 3D mammography, in which individual images of a breast are taken at different projection angles, typically within an angle of about +/−30 degrees from the vertical, and in which a 3D image is subsequently synthesized from this image information by an applicable image processing software.

DESCRIPTION OF PRIOR ART

Breast cancer is the most common type of cancer in women. According to investigations, about one in every ten women contract breast cancer at some point in their lives. When breast cancer is detected on the basis of symptoms, the illness often has already developed to a stage where the prognosis for recovery is relatively poor. Some of the cases are detected in screening programs arranged in many countries for women over the age of 40. Screening often reveals a cancer at a very early stage, so its treatment can be started in time and recovery is thus more likely.

Mammography is a widely used method in breast cancer screening as a clinical investigation method and also in follow-up diagnosis. Mammography is an X-ray imaging method wherein an apparatus specifically designed for this purpose is used. In screening studies, mammography has been reported to have a sensitivity of 90-93% and a specificity of 90-97%. This indicates that screening studies are useful and that early detection of breast cancer by screening can save human lives. It has been established that mammography reduces breast cancer mortality by 35 percent among women over 50 and by 25-35 percent among women at the age of 40-50 years.

The mammography images are examined to detect various anomalies in the breast, such as calcifications, i.e. small deposits of calcium in the soft breast tissue. A calcification generally cannot be detected by feeling the breast, but it is visible in the x-ray image. Large calcifications are generally not associated with cancer, but clusters of small calcium deposits, i.e. so-called micro-calcifications, are an indication of extra breast cell activity, which may be associated with breast cancer. Other features to be detected by mammography include cysts and fibroadenomas, which, however, are generally not associated with cancer.

In conventional screening mammography, typically the breast gland is compressed between two compression plates and exposed to radiation at least twice, from above and from an oblique direction. If necessary, additionally a third image is taken squarely from the side. As in such imaging, the tissue layers lie on top of each other in the direction of the x-ray beam, these irradiations produce two-dimensional images in which strongly absorbing structures may hinder the detection of structures lying beneath them.

Continual improvement in the mammography has led to novel type of mammography methods and devices that produce a 3D image of the patient's breast. Here, several projections of the breast at different angles are produced and a 3D distribution of it is created by using an applicable reconstruction algorithm. From the image information, i.e. the individual images, typically several images are constructed which represent layers of the breast oriented in parallel with the surface of the x-ray detector, thus making possible to detect tissue structures laying on top of each other.

A typical digital mammography apparatus comprises a frame part and a C-arm or a corresponding structure rotatably connected to the frame part. At the first end of the C-arm, there is arranged an x-ray source and at the second end, a radiation detector. A term imaging means is often used for these devices. Disposed substantially in the region between said x-ray source and detector, typically at close proximity to the detector, compression plates are arranged which are designed for positioning the breast as compressed for the duration of the exposure.

In prior art, in the context of 3D mammography, various ways to image the breast at a number of different projection angles have been used or suggested. These include continuously turning the x-ray source, with a constant or an alternating speed, along a curved path about the breast, turning the x-ray source step by step between exposures during which the x-ray source remains still, and using multiple stationary x-ray sources. As for the detector, it may be kept stationary, moved linearly and/or tilted such that it remains at right angles to the center ray of the x-ray beam for each exposure.

The x-ray source, located at the (upper) end of the C-arm, is a relatively heavy component. In the case of step-by-step movement of the x-ray source, prior to each exposure the imaging apparatus should have reached a vibration free status. Thus, the structures of the mammography apparatus should be optimized in view of the number of accelerations, decelerations and stops (stabilization times) comprised in the multi-phase imaging procedure. The overall time needed for an imaging procedure like this tends to become quite long.

On the other hand, in the case of continuous movement of the x-ray source, remarkably short exposure times, such as less than 50 ms, must be used in order to avoid creating movement artefacts. This in turn calls for using a powerful enough radiation source, which means using an even heavier x-ray source than those typically used in prior art 2D mammography apparatus and, consequently, other constructions of the imaging apparatus must be designed in view of this greater mass as well.

As for arranging several x-ray sources in a mammography apparatus, this obviously calls for a completely new type of design for a mammography apparatus in order to make it possible to implement such a specific 3D imaging modality. With this kind of a mechanical design as a basis, it would be a challenge to be able to come up with a construction that would make the apparatus practical for use in conventional 2D screening mammography as well.

SUMMARY OF THE INVENTION

The object of the current invention is focused on eliminating or reducing at least some of the problems of the imaging systems discussed above. The object of the invention is reached by the method and apparatus of the independent claims attached hereto. Some preferable embodiments of the invention are presented in the attached dependent claims.

The invention makes 3D mammography possible with the existing type of mammography apparatus, i.e. with the same kind of x-ray sources and C-arm and related construction as are typically used, by enabling the use of substantially long exposure times even though continuously moving the x-ray source during the imaging procedure. This is made possible by arranging for the breast to follow the movement of the x-ray source during at least one exposure phase of the imaging procedure. As the tomographic angle (the angle between the extreme exposure positions of the x-ray source) used in the imaging process may be of several tens of degrees, to make turning of the breast during a number of exposures possible in practise, a preferable embodiment of the procedural cycle of the invention includes a step of turning the breast back to its previous/initial position during a (each) non-exposure period of the imaging process.

One of the basic advantages of the invention is that constructing such a means in a mammography apparatus which enables repeated turning and stopping of the breast (i.e. turning and stopping of the breast holding means, such as the compression plates) during the imaging procedure is considerably simpler than arranging a corresponding movement procedure for the radiation source. In the invention, as far as the radiation source as such and the constructions for moving the radiation source are concerned, there is no need for any specific arrangements or fundamental re-design of the apparatus but the conventional design used in prior art 2D mammography may be made use of.

BRIEF DESCRIPTION OF THE DRAWINGS

In the following, some embodiments of the invention and their benefits will be described in more detail, also with help of the attached figures, of which figures

DETAILED DESCRIPTION OF THE INVENTION

Figure 1:
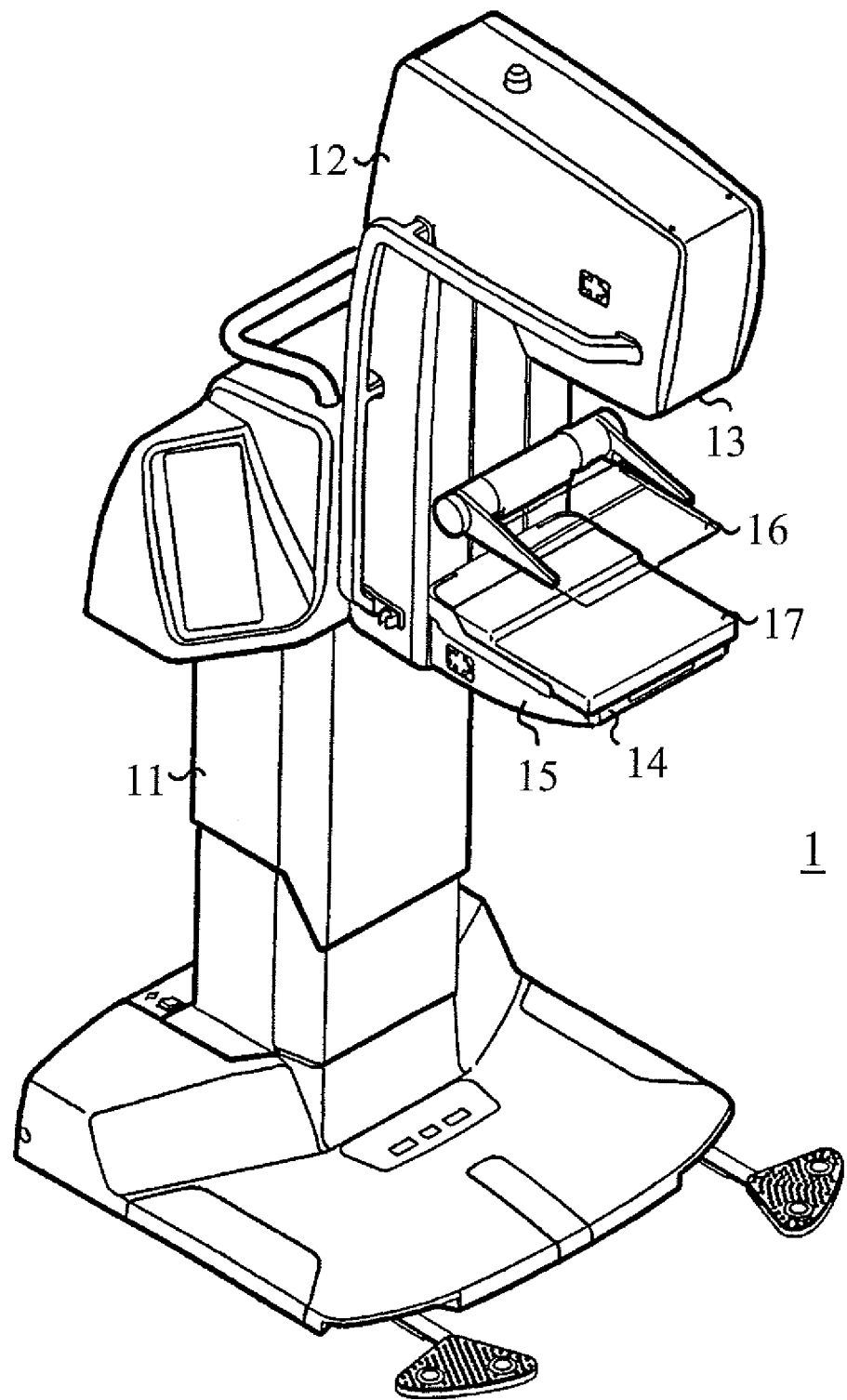
FIG. 1 represents a construction of a typical mammography apparatus.

A typical mammography apparatus 1 as presented in FIG. 1 consists of a body part 11 and a C-arm construction 12 connected to it. Typically, a radiation source 13 and an image data receiving means 15, arranged e.g. inside a so-called lower shelf structure 14, are placed at the opposite ends of the C-arm 12. These depicting means 13, 15, being located inside the cover of the apparatus, are actually not visible in FIG. 1.

Further, within the area between the depicting means 13, 15, typically in the proximity of the image data receiving means 15, a means 16, 17 for positioning/locking the object to be imaged within the imaging area has been placed. Nowadays, typically, this kind of an apparatus is motorized such that the C-arm 12 is arranged movable in a vertical direction and rotatable about an axis, typically a physical horizontal axis connecting the C-arm to the body part 11. The positioning/locking means 16, 17 typically consist of an upper compression plate 16 and a lower compression plate 17, which lower compression plate 17 may be arranged integrated with the lower shelf structure 14. Inside the lower shelf, a grid structure may be located above the image data receiving means 15, which grid structure limits entry of radiation scattered from the tissue to the image data receiving means 15. In the context of the current invention, it is in practise a necessity that the rotation axis of the C-arm 12 be arranged in such manner with respect to the location of the compression plates 16, 17 (locking means) that the patient can remain at the same position for exposures regardless of the inclination angle of the C-arm. Such a construction for this type of mammography apparatus has been taught in the European patent publication 370089.

Figure 2:
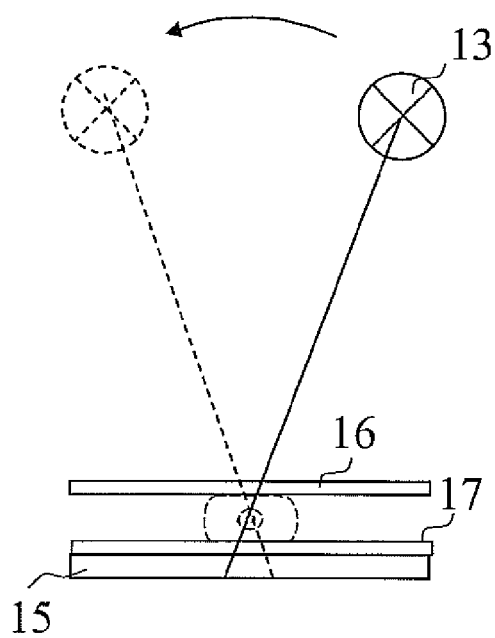
FIGS. 2a and 2b represent movements of an x-ray source of a mammography apparatus according to prior art methods to acquire image information for 3D mammography.
Figure 2:
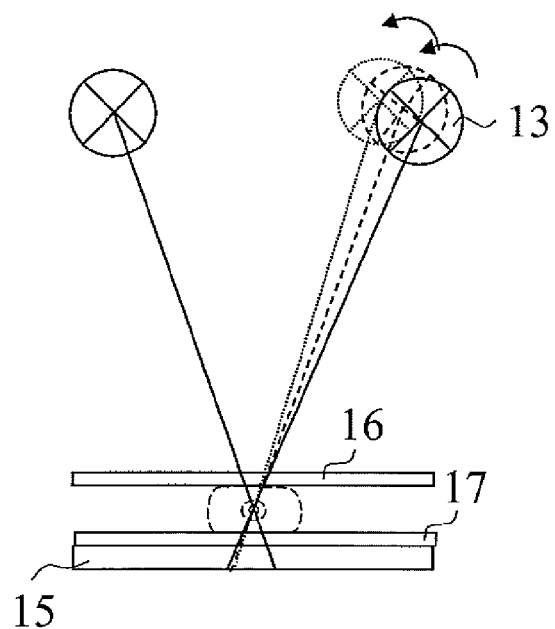

FIGS. 2a and 2b represent prior art systems to acquire image information for 3D mammography. For the sake of clarity, in FIGS. 2a, 2b, 3a, 3b not an actual cone-shaped x-ray beam originating from the focus of the x-ray source 13 but only the central ray is shown.

In the prior art system according to FIG. 2a, the x-ray source 13 is arranged to move in a continuous fashion from a starting position of the imaging procedure to an end position of the imaging procedure, and during this movement, the x-ray source 13 is energized for the duration of a number of short exposure periods, while the compression plates 16, 17 (and in FIG. 2a, also the detector 15) remain stationary. The image information detected at the detector 15 is stored and/or sent to image processing. In this kind of construction, use of a conventional anti-scatter grid is not possible as the grid would absorb a portion of the desired x-ray quanta as well at all the other exposure angles but that which is parallel with orientation of the grid lamella.

In the prior art system according to FIG. 2b, on the other hand, the x-ray source 13 is moved in a stepwise manner such that for each exposure, the x-ray source is stopped at a predefined angular position. In FIG. 2b, three such stationary exposure positions of the x-ray source 13 are shown.

Figure 3:
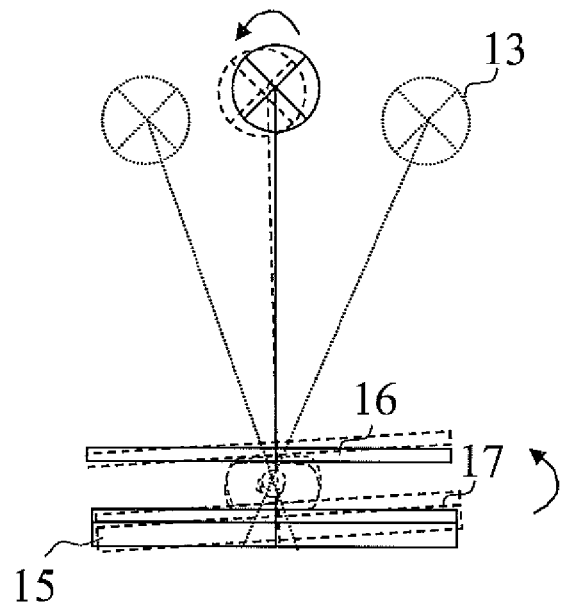
FIGS. 3a and 3b represent movements of certain constructions of a mammography apparatus according to the invention.
Figure 3:
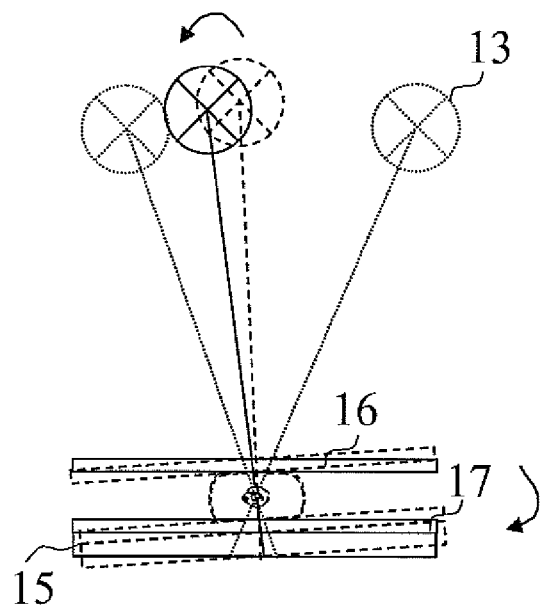

FIGS. 3a and 3b show two basic operational phases of the current mammography imaging invention. FIG. 3a can be regarded as showing one exposure phase and FIG. 3b as showing one non-exposure phase of the system, together with the extreme positions of the x-ray source 13. In these Figs, these extreme positions of the x-ray source 13 with respect to the vertical indicate the width of the tomographic angle of the system, whereas in FIG. 3a the two close to vertical positions of the x-ray source 13, and the corresponding positions of the breast locking means 16, 17 and the detector 15, depict the core operational phase of the system according to the invention, and in FIG. 3b those of a certain preferable embodiment of the invention. In the embodiment of the invention shown as a whole in FIGS. 3a and 3b, during an exposure phase (FIG. 3a), the compression plates 16, 17 are arranged to turn as synchronized with the movement of the x-ray source 13, while during a non-exposure phase (FIG. 3b), they are turned in the opposite direction. In this embodiment of the invention, the detector 15 is arranged to turn together with the compression plates 16, 17.

The synchronized movement of the x-ray source 13 and the compression plates 16, 17 according to the invention makes possible avoiding creating such movement artefacts that are always present when the breast is imaged according to a prior art method of FIG. 2a, where there is mutual movement between the x-ray source 13 and the breast during an exposure. As compared to that method, the invention also makes possible using longer exposure times and does not necessitate using an extra-powerful and thus heavier x-ray source.

On the other hand, because of not having to stop the x-ray source 13 for the duration of an (each) exposure, the time needed for the whole imaging process will be considerably shorter than that needed for a prior art process according to FIG. 2b.

As there are a number of exposures in 3D mammography, simply repeatedly turning the compression plates 16, 17 in the direction of the movement of the x-ray source 13 during each exposure period (and keeping them still during the non-exposure periods) would add up turning the compression plates 16, 17 say 15 degrees, for example, which as far as the patient is concerned would make the imaging process uncomfortable. To avoid this, preferable embodiments of the invention include an operational phase during which the x-ray source 15 is not energized (a non-irradiation period) and the compression plates 16, 17 (and the detector 15) are turned in the direction opposite to that of the movement of the x-ray source 13. According to the preferable embodiment of the invention as shown in FIG. 3b, the compression plates 16, 17 and the detector 15 are turned back to their initial position at the beginning of the preceding irradiation period.

The angle through which the compression plates 16, 17 will be turned can be arranged to be very small and the periods of non-exposure to be longer than the exposure periods so that there will be plenty of time to establish a stable starting situation for a subsequent exposure period. In other words, according to preferable embodiments of the invention, there will be plenty of time for counter-turning the breast as the periods when the x-ray source 13 is not energized are arranged to be considerably longer than the periods during which it is energized. Thinking of an example of having a typical prior art mammography apparatus and using 12 exposures starting at intervals of 5 degrees, the compression plates 16, 17 could be turned through 2 degrees or even less, which would easily leave enough time for backwards turning even when taking into account the time needed for acceleration and deceleration of the movements.

As shown in FIG. 3a, in one preferable embodiment of the invention, both the radiation source 13 and the image detector 15 are moved at the same essentially regular angular velocity around the breast whilst it is compressed between the compression plates 16, 17—or locked otherwise in a means arranged for this purpose.

In practise, regarding embodiments of the invention as shown in FIGS. 3a and 3b, it is essential that the compression plates 16, 17, or said other locking means for the breast, are arranged to turn at a short distance from the rotation centre of the radiation source 13 for the most, since during the imaging procedure according to the invention, it would be impossible to reposition the patient for irradiations at different projection angles.

According to a specific preferable embodiment of the invention, first, during exposure of each of the projection images, the compression plates 16, 17, or said other locking means, are turned as synchronized with the movement of the radiation source 13. Thus, the breast will remain still with respect to the radiation source 13 during each such irradiation period. Then, second, between the irradiation periods, the compression plates 16, 17 are turned back to their position at the beginning of the preceding irradiation period. As a consequence, the total angle the locking means 16, 17 shall turn needs to be only as small as the angle of turn needed for creating synchronization of movements during an individual exposure of one projection image. This angle may be arranged to be e.g. less than 2 degrees, such as 0.5-2 degrees, which in view of the strain to a patient will be tolerable. Thus, even when taking into account the required accelerations and decelerations, as discussed, in case images are taken at 5 degree intervals, for example, over a tomographic angle of say 50 degrees, there will still be plenty of time for returning the locking means (e.g. upper and lower compression plate 16, 17) back to their initial position at the beginning of an exposure phase.

More generally speaking, in the system according to the invention, the breast to be imaged is arranged locked in a locking means 16, 17 and during the imaging process, an x-ray source 13 is moved with respect to the location of the breast to be imaged and the breast is irradiated during a number of irradiation periods which begin at a number of angular positions of the x-ray source 13. During the imaging process, the x-ray source 13 is moved continuously and the breast is irradiated during a number of short irradiation periods and, during a period when the breast is being irradiated, the locking means 16, 17 is moved as synchronized with the movement of the x-ray source 13. Regarding a mammography apparatus according to the invention, it comprises a body part 11 and arranged thereto an x-ray source 13, an image detector 15 as well as within an area between the x-ray source 13 and the image detector 15, a means arranged for locking a breast 16, 17, the x-ray source 13 being arranged movable with respect to the location of said locking means 16, 17. Further, the apparatus comprises a control system arranged to control operation of the apparatus. The locking means 16, 17 is arranged turnable and movement of the locking means 16, 17 and the x-ray source 13 is arranged motorised and the operation of the x-ray source controlled by said control system such that during an imaging process, the x-ray source 13 moves continuously and the breast is irradiated during a number of short irradiation periods and, during an irradiation period, said locking means 16, 17 turns as synchronized with the movement of the x-ray source 13.

The imaging procedure may include a phase prior to the first irradiation period wherein said locking means 16, 17 is turned in a direction opposite to that when moved as synchronized with the movement of the x-ray source 13. There may be periods of backwards movement of the locking means 16, 17 in between any number of successive irradiation periods. The length of the turning-back movement of the locking means 16, 17 (and possibly also that of the image detector 15) may be either exactly the same as during an exposure period, i.e. the locking means 16, 17 may be moved back to its initial position at the beginning of a preceding exposure period, or the backwards movement may be shorter or longer than the one having taken place during a preceding exposure. The length of the backwards movement does not have to be any exact multiple of the steps of the movement during an exposure. As an exemplary embodiment of the invention, the imaging procedure may consist of steps of two exposure periods between which the locking means 16, 17 do not turn in any direction, but after the second of these exposure periods, the backwards movement will correspond to the total movement of the locking means 16, 17 during these two exposure periods.

The extreme positions of the x-ray source 13 with respect to the breast during the imaging process may be arranged to make up a tomographic angle of several tens of degrees, such as about 50 degrees. In one preferable embodiment, the overall movement of the x-ray source 13 is arranged to be symmetrical with respect to the vertical, i.e. the overall tomographic angle to be about plus-minus 25 degrees with respect to the vertical. Preferably, the movement of the x-ray source 13 is arranged to follow a curved path as in the case of typical existing mammography apparatus, yet the principle of the invention may be realized also when moving the x-ray source linearly.

Considering the angles from another point of view, the ratio between the angle of the minute individual turns of the locking means 16, 17 during exposure periods with respect to the overall displacement of the x-ray source 13 may be arranged to be of the order of 1/10. The imaging procedure may be arranged to consist of about 11-15 exposure periods.

Even though varying breast thicknesses and the desired velocity of the x-ray source 13 may affect what is optimal, preferable embodiments of the invention include using an x-ray source 13 comprising a tungsten anode which, with proper arrangements such as using a selenium based imaging detector and especially a silver filter of proper thickness to absorb those low energy x-ray quanta which would not be able to penetrate the breast tissue, can result in a reduced radiation dose when compared to some other arrangements. In the context of preferable embodiments of the invention, exposure times for the projection images of around 50-100 ms may be used, and imaging parameter values for the x-ray tube voltage of around 35-40 kV, even up to 45 kV, and about 5 mAs. With kV values of about 30-34, mAs values of about 10-13 may be used.

Figure 4:
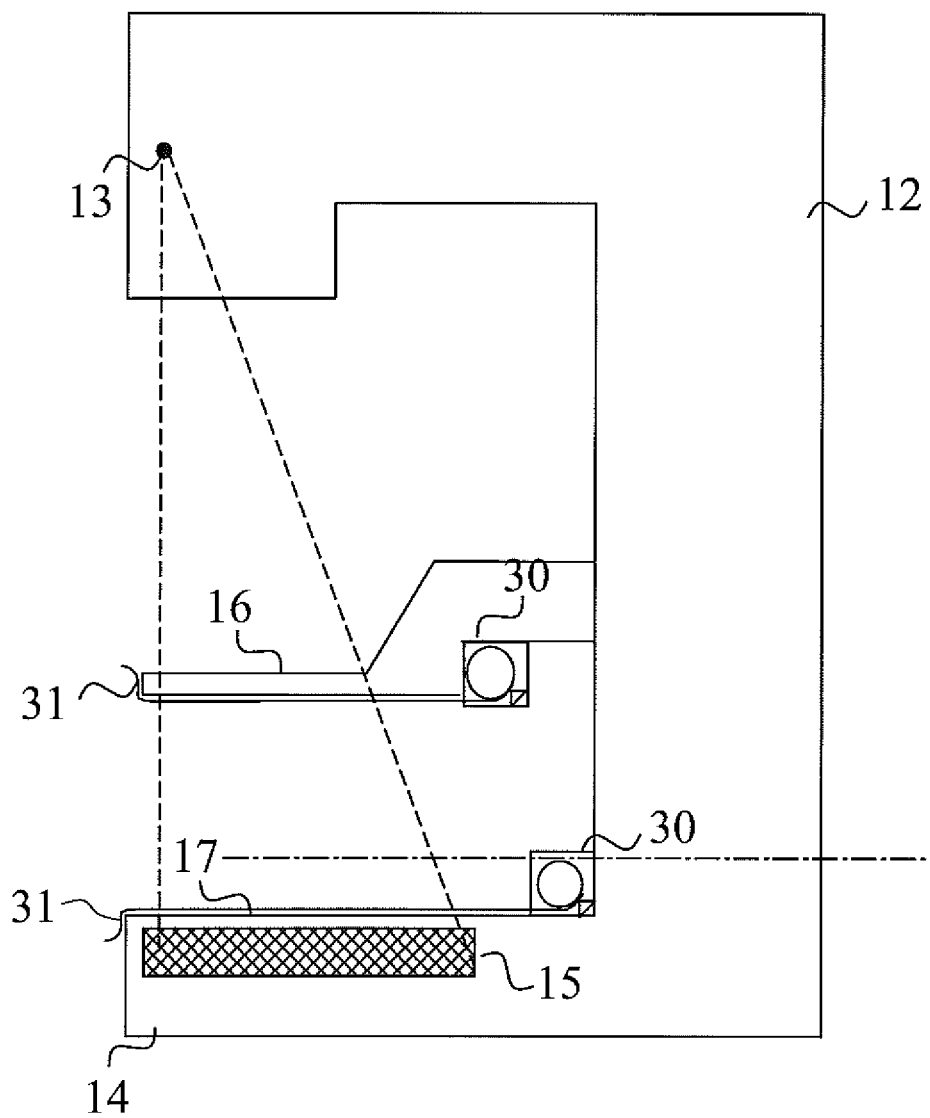
FIG. 4 represents a C-arm of a mammography apparatus fitted with an arrangement for drawing tissue into the volume between compression plates of the apparatus.

One preferable embodiment of the invention includes an arrangement in which in functional connection with the locking means, there has been arranged a means for pulling tissue into the space between the compression plates 16, 17. Such a means may be arranged to comprise e.g. an arrangement as shown in FIG. 4, wherein an upper and a lower stretching device are integrated with both of the compression plates 16, 17. The stretching devices 30 may be arranged to comprise a means for engaging and pulling a stretching means, such as a plastic sheet 31, so that in connection with compressing the breast between the compression plates 16, 17, breast tissue will be drawn in between the compression plates 16, 17 upon positioning of the breast for imaging. Such an arrangement enables using perhaps 10% less compression in the context of the current invention than typically used in the art of mammography, which makes the imaging procedure including both compressing and turning a breast less awkward.

The current invention is applicable for use both in the context of so called full-field sized and smaller imaging detectors used in mammography.

The invention claimed is:

1. A mammography imaging method in which a breast to be imaged is arranged locked in a locking means 16, 17 within an area between an x-ray source 13 and an image detector 15 of a mammography apparatus and in which during the imaging process, the x-ray source 13 is moved with respect to location of the breast and the breast is irradiated at a number of angular positions of the x-ray source 13 with respect to location of the breast, characterized in that, during the imaging process, the x-ray source 13 is moved continuously and the breast is irradiated during a number of short irradiation periods and not irradiated during a number of non-irradiation periods between the irradiation periods and, during an irradiation period, said locking means 16, 17 is turned as synchronized with the movement of the x-ray source 13 so that the breast remains still with respect to the moving x-ray source 13, and during a non-irradiation period, said locking means 16, 17 is not turned as synchronized with the movement of the x-ray source 13 so that the breast does not remain still with respect to the moving x-ray source 13.

2. The method according to claim 1, wherein prior to the first irradiation period, and/or in between any number of subsequent irradiation periods, that is during a period when the breast is not being irradiated, said locking means 16, 17 is turned in a direction opposite to that when turned as synchronized with the movement of the x-ray source 13.

3. The method according to claim 1 wherein after an irradiation period during which said locking means 16, 17 is moved as synchronized with the movement of the x-ray source 13 and prior to at least one subsequent irradiation period, said locking means 16, 17 is turned at least substantially back to its initial position, i.e. at least substantially to its position at the beginning of said preceding irradiation period.

4. The method according to claim 1 wherein the imaging process includes a number of irradiation periods during which said locking means 16, 17 is turned as synchronized with the movement of the x-ray source 13, and during each non-irradiation period subsequent to such irradiation periods, the locking means 16, 17 is turned at least substantially back to its position at the beginning of such preceding irradiation period.

5. The method according to claim 1 wherein the movement of the locking means 16, 17 during an irradiation period includes turning the locking means 16, 17 for an angle through 2 degrees or less, such as through 0.5-2 degrees.

6. The method according to claim 1 wherein the extreme angular positions of the x-ray source 13 with respect to the breast during the imaging process make up a tomographic angle of several tens of degrees.

7. The method according to claim 1 wherein the overall movement of the x-ray source 13 is arranged to be symmetrical with respect to a vertical.

8. The method according to claim 1 wherein the movement of the x-ray source 13 is arranged to follow a curved path about the breast.

9. The method according to claim 1 wherein the locking means 16, 17 comprises compression plates 16, 17 between which a breast is compressed for the duration of the imaging process, and/or a stretching means 30, 31 is arranged to be used for drawing breast tissue in between the locking means 16, 17/the compression plates 16, 17.

10. The method according to claim 1 wherein during an irradiation period, the x-ray source 13 is operated depending on the breast tissue characteristics by using imaging parameter values for the x-ray tube including a tungsten anode of about 35-45 kV and about 5 mAs, or about 30-34 kV and 10-13 mAs.

11. The method according to claim 1 wherein the method includes about 11-15 irradiation periods and/or a ratio between the angle through which the locking means 16, 17 is turned during an irradiation period and the total tomographic angle of the imaging process is less than $\frac{1}{10}$.

12. A mammography apparatus comprising a body part 11 and arranged thereto an x-ray source 13, an image detector 15 as well as within an area between the x-ray source 13 and the image detector 15, a means arranged for locking a breast 16, 17, the x-ray source 13 being arranged movable with respect to location of said locking means 16, 17, the apparatus further comprising a control system arranged to control operation of the apparatus, characterized in that said breast locking means 16,17 is arranged turnable and movement of the locking means 16, 17 and the x-ray source 13 is arranged motorised and operation of the x-ray source controlled by said control system such that during an imaging process, the x-ray source 13 moves continuously and the breast is irradiated during a number of short irradiation periods and not irradiated during a number of non-irradiation periods between the irradiation periods and, during an irradiation period, said locking means 16, 17 turns as synchronized with the movement of the x-ray source 13 so that the breast remains still with respect to the moving x-ray source 13, and during a non-irradiation period, said locking means 16, 17 is not turned as synchronized with the movement of the x-ray source 13 so that the breast does not remain still with respect to the moving x-ray source 13.

13. The mammography apparatus according to claim 12, wherein the control system is arranged to control operation of the apparatus such that prior to the first irradiation period, and/or in between any number of subsequent irradiation periods, that is during a period when the breast is not being irradiated, said locking means 16, 17 turns in a direction opposite to that when turning as synchronized with the movement of the x-ray source 13.

14. The mammography apparatus according to claim 12 wherein the control system is arranged to control operation of the apparatus such that after an irradiation period during which said locking means 16, 17 is moved as synchronized with the movement of the x-ray source 13 and prior to at least one subsequent irradiation period, said locking means 16, 17 turns at least substantially back to its initial position, i.e. at least substantially to its position at the beginning of said preceding irradiation period.

15. The mammography apparatus according to claim 12 wherein the control system is arranged to control operation of the apparatus such that there are a number of irradiation periods during which said locking means 16, 17 turns as synchronized with the movement of the x-ray source 13, and during each of the non-irradiation periods subsequent to such irradiation periods, the locking means 16, 17 turns at least substantially back to its position at the beginning of such preceding irradiation period.

16. The mammography apparatus according to claim 12 wherein the control system is arranged to control operation of the apparatus such that the locking means 16, 17 turns during an irradiation period through an angle of 2 degrees or less, such as through 0.5-2 degrees.

17. The mammography apparatus according to claim 12 wherein the movement of the x-ray source 13 is arranged to follow a curved path about a breast positioned in the breast locking means 16, 17.

18. The mammography apparatus according to claim 12 wherein the locking means 16, 17 comprises compression plates 16, 17 between which a breast is compressed for the duration of the imaging process and/or a stretching means 30, 31 has been arranged to the apparatus for pulling breast tissue in between the locking means 16, 17/the compression plates 16, 17.

* * * * *